United States Patent
Uematsu et al.

(10) Patent No.: US 6,225,064 B1
(45) Date of Patent: May 1, 2001

(54) METHOD FOR ASSAYING DNA FRAGMENTS IN MIXTURE

(75) Inventors: Chihiro Uematsu, Kawasakii; Hideki Kambara, Hachiouji; Kazunori Okano, Shiki, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/413,814

(22) Filed: Oct. 7, 1999

(30) Foreign Application Priority Data

Oct. 8, 1998 (JP) .................................................. 10-286286

(51) Int. Cl.⁷ ................................................. C12Q 1/68
(52) U.S. Cl. .......................... 435/6; 435/91.1; 435/91.2; 435/172.3; 435/320.1; 536/23.1; 536/25.4
(58) Field of Search ............................ 435/6, 91.2, 172.3, 435/320.1; 536/23.1, 25.4

(56) References Cited

U.S. PATENT DOCUMENTS

| | | | |
|---|---|---|---|
| 5,545,527 | * | 8/1996 | Stevens et al. ............................ 435/6 |
| 5,759,822 | * | 6/1998 | Chenchik et al. ................... 435/91.2 |
| 6,060,240 | * | 5/2000 | Kamb et al. .............................. 435/6 |

OTHER PUBLICATIONS

FDD Display, FEBS Letters, 351, 1994, pp. 231–236.
Nucleic Acids Research, 24, 1996, pp. 2616–2617.
Nucleic Acids Symposium Series, 35, 1996, pp. 257–258.
Biopolymers, 3, 1995, pp. 195–208.
Proceedings of National Academy of Science, USA, 83, 1986, pp. 3746–3750.

\* cited by examiner

*Primary Examiner*—W. Gary Jones
*Assistant Examiner*—Janell E. Taylor
(74) *Attorney, Agent, or Firm*—Mattingly, Stanger & Malur, P.C.

(57) ABSTRACT

The inventive method for assaying DNA fragments in mixture comprises step 1 of ligating different oligomers hybridizable to primers of the same melting temperature and the same length to individual groups of DNA fragments in a set of DNA fragments;

step 2 of mixing together the groups of DNA fragments ligated with the oligomers;

step 3 of simultaneous PCR of the groups of DNA fragments ligated with the oligomers in one receptacle by using the primers being complementary to the oligomers and corresponding to the individual groups; and step 4 of detecting PCR amplified DNA fragments; characterized in that the method enables the comparison of plural samples under no influence of PCR reproducibility.

4 Claims, 7 Drawing Sheets ns of DNA fragments expressed on the electrophoresis pattern recovered by using the primers of the individual sets, the whole information of each expressed gene can be recovered. Consequently, the type of each expressed gene and the expression level thereof can be identified.

METHOD FOR ASSAYING DNA FRAGMENTS IN MIXTURE

BACKGROUND OF THE INVENTION

The present invention relates to a method for amplifying nucleic acid, a method for assaying DNA fragments in mixture, a method for assaying RNA fragments in mixture, and an expression profiling process of a group of expressed genes; more specifically, the invention relates to a method for assaying DNA fragments by gel electrophoresis and by using fluorophore label.

The nucleotide sequence of a gene or a DNA can be compared with other nucleotide sequences by DNA sequencing, but it is very difficult to determine the sequence of a long DNA or a mixture sample of a great number of DNA fragments. So as to determine the sequence of such long DNA, therefore, the long DNA is first fragmented; then, the resulting DNA fragments are assayed on gel electrophoresis patterns. Due to the recent progress of various assay methods and apparatuses therefor, numerous expressed genes can simultaneously be detected and assayed.

The expression profiling method includes for example a scanning process based on gel electrophoresis. The scanning process includes FDD [Fluorescent Differential Display; FEBS Letters 351, 231–236 (1994)] and a process using terminal nucleotide selective primer [Nucleic Acids Research, 24, 2616–2617 (1996); Nucleic Acids Symposium Series, No. 35, 257–258 (1996)].

All these scanning processes comprise PCR (Polymerase Chain Reaction) using plural primers in common to plural DNA fragments along with a sample cDNA or mRNA as template and recovering gene expression information based on the electrophoresis patterns of the resulting PCR products. Because the expression can be detected with no use of any gene-specific probe according to the scanning processes, advantageously, the expression profile of a gene with a nucleotide sequence not yet identified can be yielded.

The process using terminal nucleotide selective primer comprises digesting a double-stranded cDNA with a restriction enzyme and ligating an oligonucleotide with a known nucleotide sequence at the terminus of a DNA fragment as a digestion product. PolyA tail is generally present at the 3' terminus of cDNA. Because a nucleotide sequence between the polyA tail at the 3' terminus of the cDNA and the ligated oligonucleotide is specific to the cDNA, a DNA fragment carrying the nucleotide sequence is assayed as a fragment representing (or identifying) the cDNA.

Because gene species of several thousands to several ten thousands in number are expressed in living organisms, the types of such cDNA representative fragments are so numerous that these representative fragments cannot be separated and assayed in one lane by electrophoresis. Thus, all these types of such representative fragments are divided in plural groups, whereby the number of such DNA fragments included in each one group is sufficiently reduced such that the DNA fragments in each one group can be separated and assayed satisfactorily by gel electrophoresis. So as to divide all the representative fragments in plural groups, PCR primers with a selective nucleotide sequence composed of two nucleotides at the 3' terminus thereof are used. By PCR, DNA fragments with terminal two nucleotides complementary to each selective nucleotide sequence are amplified. From two primer sets with two selective nucleotide sequences is selected each one primer; subsequently, a group of a combination of appropriate two primers is prepared.

By PCR with primers of the individual sets, the resulting amplified products are assayed by electrophoresis. Via combinations of DNA fragments expressed on the electrophoresis pattern recovered by using the primers of the individual sets, the whole information of each expressed gene can be recovered. Consequently, the type of each expressed gene and the expression level thereof can be identified.

For fragment assay, at least one primer of oligo dT primer and a primer complementary to the oligomer ligated at the terminal digestion site of a DNA fragment is labeled with fluorophore; using the primer labeled with the fluorophore, the DNA fragment is amplified in such a number above the detection sensitivity of an assay apparatus such as fluorescent DNA sequencer and the like.

SUMMARY OF THE INVENTION

Conventional expression profiling processes based on electrophoresis have various drawbacks as described below in practical sense. By the processes on the basis of electrophoresis, the resulting comparative results are at serious error if the reproducibility of PCR amplification is low.

For comparing the difference in expression profile between plural samples, the samples each are independently subjected to PCR and the resulting PCR products are then electrophoresed. The results are compared to each other. Plural samples labeled with the same fluorophore species are subjected to PCR in different reaction tubes; and the resulting PCR products are assayed in different electrophoresis lanes. Plural samples labeled with different fluorophore species are independently subjected to PCR in different tubes; and the resulting products are assayed in one electrophoresis lane. According to the conventional processes, sample preparation for electrophoresis requires PCR in different tubes, so PCR reproducibility influences the precision of the comparison of the electrophoretic assay results of PCR products. Currently, nevertheless, PCR reproducibility is disadvantageously insufficient.

It is an object of the present invention to provide a method for assaying DNA fragments in mixture, comprising PCR in one reaction tube, thereby enabling an expression profiling process of comparing plural samples together, under no influence of PCR reproducibility.

According to the inventive method for assaying DNA fragments in mixture, each sample requires a PCR primer with a different nucleotide sequence but of the same length and the same melting temperature ($T_m$), for reaction of plural samples in one tube. Each primer corresponding to each of plural samples is of a nucleotide sequence, with no chance of secondary structure formation between these primers, so that these primers can independently function and never influence the reaction of other primers. Plural DNA samples are placed in one reaction tube for PCR, whereby variation of each PCR can be eliminated.

So as to amplify a first DNA sample with a primer of a first primer set and amplify a second DNA sample with a primer of a second primer set, an oligonucleotide with a complementary nucleotide sequence to each primer is ligated to the primer. So as to identify the primers serving for amplification, the primer of the first primer set and the primer of the second primer set are labeled with different fluorophore species. Because plural DNA samples are amplified by using the primers of plural primer sets in one tube, no problem concerning PCR reproducibility occurs.

In order to compare together DNA fragments amplified with the primers of plural primer sets, the difference in reaction reactivity between these primers should be eliminated. $T_m$ value of primer, $T_m$ value of sample DNA, and $T_m$ value of PCR amplified product determine the PCR reaction efficiency.

Expression of one gene in plural sample DNAs means that the sample DNAs with relation to the gene and the PCR amplified products thereof are identical; thus, the $T_m$ values thereof are equal. Hence, the PCR reaction efficiency depends on the $T_m$ value of primer. By setting the $T_m$ values of plural primers at an equal value, the resulting PCR reaction efficiencies can be retained equally.

The $T_m$ value of DNA can be calculated, approximately, depending on the nucleotide species composing the DNA sequence [Biopolymers, 3, 195–208 (1965)]. The $T_m$ value can be calculated by using the difference in stacking between a nucleotide species and a nucleotide adjacent thereto. By using a nucleotide sequence composed of an interesting nucleotide and one nucleotide adjacent thereto, the $T_m$ value can be more accurately calculated [Proc. Natl. Acad. Sci. USA, 83, 3746–3750 (1986)].

So as to prepare plural primers at an equal $T_m$ value, the individual primers are allowed to comprise a nucleotide sequence of several species of modules, each module being composed of 4 to 6 nucleotides. For example, 5 modules (A, B, C, D, and E), each module being composed of 4 nucleotides, are aligned sequentially in the order A-B-C-D-E to prepare a primer with the nucleotide sequence or in the order C-D-A-B-E to prepare a primer with the latter nucleotide sequence. Herein, each of the individual modules comprises the same nucleotide species at both the termini thereof. Even if these modules that have same nucleotide species at the both termini are shuffled together in order, the nucleotide sequence in the linking region between the modules is never modified because the nucleotides at both the termini are identical. Thus, no effect of the change of the sequence order of these modules is reflected on the $T_m$ value.

The nucleotide composition composing each primer in its entirety is never changed because only the order of these modules is modified in each primer. As has been described above, almost no difference is found in the $T_m$ values of individual primers with modified sequence orders of modules or in PCR reaction efficiency. Additionally because module-shuffling primers are not complementary to each other, these primers together never form a double strand to suppress PCR.

By aligning several modules in various fashions wherein each of the individual modules comprises the same nucleotide at both the termini thereof, plural primers with no difference in PCR reaction efficiency can be prepared. Because PCR is effected in one reaction tube, the variation of PCR reaction efficiency can be eliminated.

The inventive method for assaying DNA fragments in mixture comprises PCR of plural samples in one reaction tube by using primers with nucleotide sequences different from each other and at the same length and the same melting temperature, namely the same $T_m$ value, under no influence of the variation of PCR reaction efficiency, to quantitatively compare the ratio of DNA fragments present in plural samples.

The inventive method for assaying DNA fragments in mixture comprises step 1 of ligating different oligomers hybridizable to primers of the same melting temperature and the same length to individual groups of DNA fragments in a set of DNA fragments;

step 2 of mixing together the groups of DNA fragments ligated with the oligomers;

step 3 of simultaneous PCR of the groups of DNA fragments ligated with the oligomers in one receptacle by using the primers being complementary to the oligomers and corresponding to the individual groups; and step 4 of detecting PCR amplified DNA fragments.

The inventive method for assaying DNA fragments in mixture is characteristic as follows.

1. The primers corresponding to the individual groups are labeled with fluorophores different from each other in a corresponding manner to the individual groups, to serve for the detection of electrophoresed DNA fragments labeled with the fluorophores after PCR amplification.
2. The PCR amplified DNA fragments are detected by using a DNA probe array immobilizing plural types of DNA probes of nucleotide sequences complementary to the individual groups of DNA fragments thereon.
3. The primers corresponding to the individual groups are labeled with different fluorophores, correspondingly to each of the individual groups.
4. The primers comprise plural module sequences, each module sequence being composed of 4 to 6 nucleotides, wherein the order of plural module sequences varies, depending on each of the groups, while the plural module sequences comprise the same nucleotide species at the 3' terminus and 5' terminus thereof.
5. The primers corresponding to the individual groups are composed of a 10- to 25-nucleotide common nucleotide sequence in common to the individual primers for the individual groups and a selective nucleotide sequence being composed of one to 3 nucleotides and recognizing the DNA fragments of the individual groups, wherein the common nucleotide sequence comprises plural module sequences in orders varying, depending on the individual groups, each module sequence being composed of 4 to 6 nucleotides and wherein the selective nucleotide sequence includes all nucleotide sequences of combinations of one to 3 nucleotides.

The inventive primers are used for the method for assaying DNA fragments in mixture; the primers comprise plural module sequences in orders varying, depending on the individual groups, each module sequence being composed of 4 to 6 nucleotides, while the plural module sequences comprise the same nucleotide species at the 3' terminus and 5' terminus thereof.

According to the method for assaying DNA fragments in mixture, the inventive primers corresponding to the individual groups characteristically comprise the 10- to 25-nucleotide common nucleotide sequence in common to the primers of the individual groups, and the selective nucleotide sequence being composed of one to 3 nucleotides and recognizing the DNA fragments of the individual groups, wherein the common nucleotide sequence comprises plural module sequences in orders varying, depending on the individual groups, each module sequence being composed of 4 to 6 nucleotides and wherein the selective nucleotide sequence includes all nucleotide sequences of combinations of one to 3 nucleotides and the plural module sequences comprise the same nucleotide species at the 3' terminus and 5' terminus thereof.

Furthermore, the inventive primers are plural primers of different nucleotide sequences for use in PCR, wherein the primers comprise different orders of plural module sequences composed of plural nucleotides and the plural primers thus comprising such different orders of plural module sequences are of the same melting temperature and wherein the plural module sequences comprise the same nucleotide species at the 3' terminus and 5' terminus thereof.

Still furthermore, the inventive primer sets are plural primer sets of plural primers with different nucleotide sequences for use in PCR, wherein each primer set is composed of a 10- to 25-nucleotide common nucleotide sequence in common to the primers of each primer set and a selective nucleotide sequence being composed of one to 3 nucleotides and recognizing DNA fragments derived from sample DNA, wherein the common nucleotide sequence comprises plural module sequences in orders varying, depending on each primer set, each module sequence being composed of 4 to 6 nucleotides and wherein the selective nucleotide sequence includes all nucleotide sequences of combinations of one to 3 nucleotides; the plural module sequences comprise the same nucleotide species at the 3' terminus and 5' terminus thereof; and the plural primers of the plural primer sets are of the same melting temperature.

In accordance with the invention, plural primers comprising different orders of plural module sequences are used to prepare plural primers at the same $T_m$ value. For PCR amplification of plural sample DNAs and comparison of the resulting PCR products, consequently, DNAs or RNAs extracted from plural samples can be PCR amplified in one reaction tube and the resulting PCR products can be assayed in one electrophoresis lane. Because laborious reaction procedures can be saved, with no PCR variation in various reaction tubes, the precision of comparison can be improved with no concern of PCR reproducibility in the conventional art.

With reference to FIG. 1, a representative composition of the invention will be schematically described below. The inventive method for assaying DNA fragments in mixture and capable of expression profiling, comprises step 1 of ligating different oligomers 11, 12 hybridizable to primers 21, 22 of the same melting temperature and the same length to groups of DNA fragments 3, 4 in a set of DNA fragments;

step 2 of mixing together the groups of DNA fragments 5, 6 ligated with the oligomers 11, 12;

step 3 of simultaneous PCR of the groups of DNA fragments 5, 6 ligated with the oligomers 11, 12 in one receptacle 29 by using the primers 21, 22 being complementary to the oligomers 11, 12 and corresponding to the individual groups; and step 4 of detecting PCR amplified DNA fragments by electrophoretic separation. The above composition enables comparison of plural samples, under no influence of PCR reproducibility.

DESCRIPTION OF THE PREFERRED EMBODIMENTS

EXAMPLE 1

Figure 1:
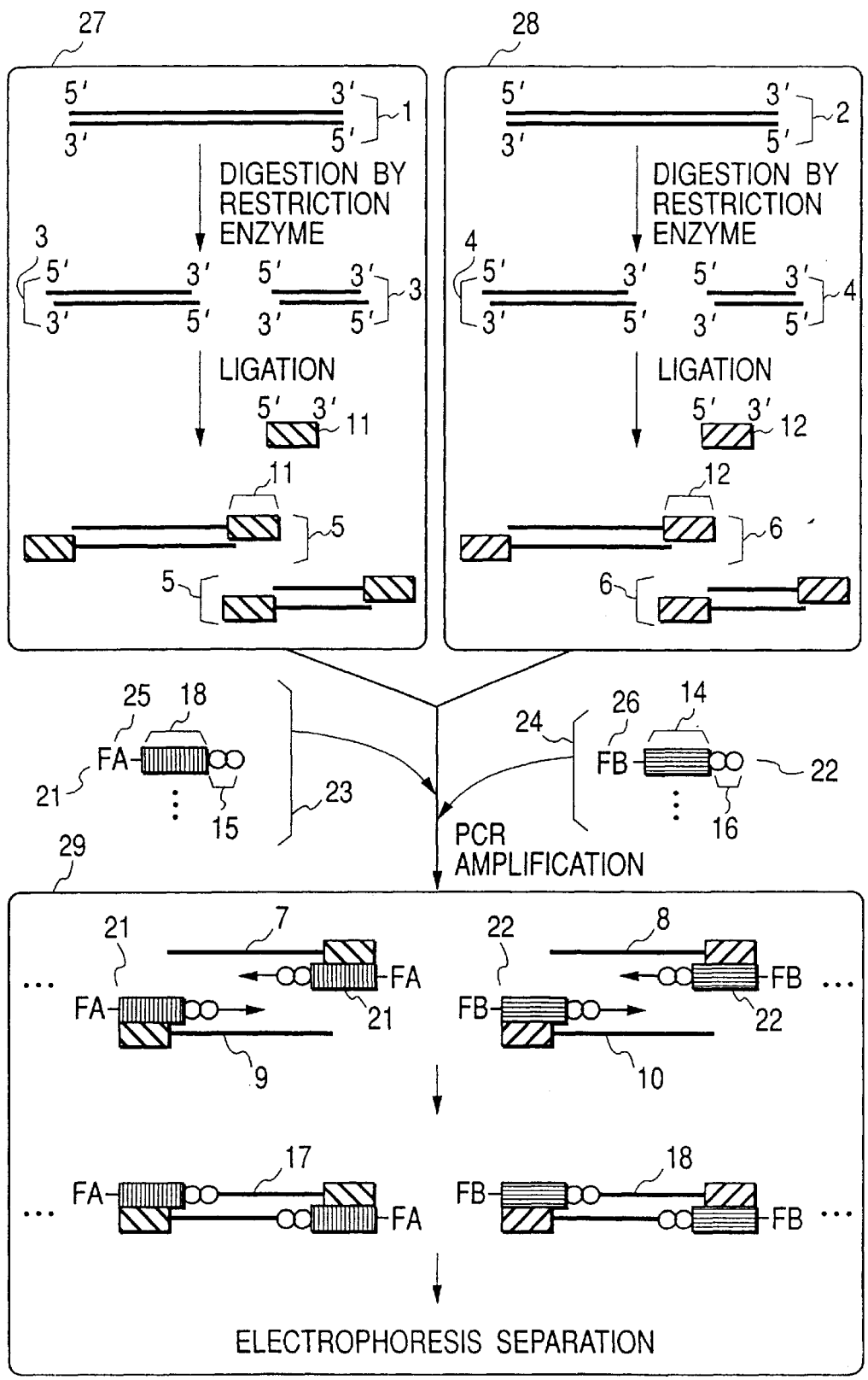
FIG. 1 is a flowchart of the procedures of the expression profiling of Example 1 in accordance with the invention.

FIG. 1 is a flowchart depicting the procedures of the expression profiling of Example 1 in accordance with the invention. The sample cDNAs were prepared from the RNAs extracted from rat liver and rat kidney. From the cells homogenized in a conventional manner were extracted RNAS by the guanidium thiocyanate method. The extracted RNAs were converted to cDNAs by using reverse transcriptase, which were designated as sample cDNAs (rat liver-derived cDNA and rat kidney-derived cDNA).

As shown in FIG. 1, rat liver-derived sample cDNA 1 (in a mixture of various cDNAs; one cDNA is shown in the figure) was digested with a class II restriction enzyme in reaction tube 27 to prepare cDNA fragment 3. In the same manner, rat kidney-derived sample cDNA 2 was digested with the same restriction enzyme as used for the digestion of the sample cDNA 1 to prepare cDNA fragment 4 (in a mixture of various cDNAs; one cDNA is shown in the figure). Sau3A I recognizing the nucleotide sequence 5'-GATC-3' to digest the site ↓GATC was used as the class II restriction enzyme. The class II restriction enzyme recognizing four nucleotides is preferable and includes for example Nla III and Hha I. Restriction enzymes recognizing six nucleotides may also be satisfactory, including Hind III and EcoR I.

By ligating oligonucleotide 11 with a known nucleotide sequence at the digestion site of the cDNA fragment 3 by ligation, cDNA fragment 5 with the oligonucleotide 11 with the known nucleotide sequence ligated at the 3' terminus thereof is recovered. By ligating oligonucleotide 12 with a known nucleotide sequence at the digestion site of the cDNA fragment 4 in another reaction tube 28 by ligation, cDNA fragment 6 with the oligonucleotide 12 with the known nucleotide sequence ligated at the 3' terminus thereof is recovered.

By subsequently mixing together the cDNA fragment 5 and the cDNA fragment 6 to prepare a mixture solution, a part of the solution is placed in PCR tube 29 for use as template DNA fragment for PCR.

Primer 21 composed of four module sequences, namely I. TCAT, II. CACC, III. TTCT and IV. CCAC, the restriction enzyme recognition nucleotide sequence GATC, and selective nucleotide sequence NN 15 being composed of two nucleotides NN (independently corresponding to any one of A, C, G and T) and recognizing two nucleotides subsequent to the 5' terminus (G) of the restriction enzyme recognition nucleotide sequence GATC is prepared.

Among the nucleotides composing the sequence of each module, the nucleotide species at both the termini of each of the individual modules are the same so as to avoid the modification of the nucleotide sequence at the module-linking parts even if the order of the modules that have same nucleotide sequence at both the termini is modified. The nucleotide sequence of the primer 21 (SQ ID No. 1) is composed of common nucleotide sequence 13 composed of the module sequence in the order of I-II-III-IV and the restriction enzyme recognition nucleotide sequence GATC, and the selective nucleotide sequence NN 15 composed of two nucleotides.

SQ ID No. 1
5'-TCATCACCTTCTCCACGATCNN-3'

NN corresponds to any one of A, C, G and T; the primer 21 composes primer set 23 composed of 16 primers.

Furthermore, primer 22 composed of, the common nucleotide sequence 14 composed of four module sequences aligned in the order of III-IV-I-II and restriction enzyme recognition nucleotide sequence GATC, and selective nucleotide sequence NN 16 composed of two nucleotides NN (NN corresponding to any one of A, C, G and T) is prepared as shown as the nucleotide sequence of SQ ID No. 2. NN corresponds to any one of A, C, G and T, and the primer 22 composes primer set 24 composed of 16 primers, like the primer 21.

SQ ID No. 2
5'-TTCTCCACTCATCACCGATCNN-3'

The oligonucleotide 11 of a known nucleotide sequence is complementary to the sequence of the modules in the order of I-II-III-IV in the primer 21 belonging to the primer set 23. The oligonucleotide 11 is ligated in the digestion site of the cDNA fragment 3 as a digestion product with the restriction enzyme Sau3A I recognizing the nucleotide sequence 5'-GATC-3' to digest the site ↓GATC. The oligonucleotide 11 is ligated in the 3' terminus of the sequence of the 4 nucleotides, namely 5'-GATC-3' at the 3' terminus of the −strand of the cDNA fragment 3 and in the 3' terminus of the sequence of the 4 nucleotides, namely 5'-GATC-3' at the 3' terminus of the+strand of the cDNA fragment.

The primer set 23 hybridizes to the restriction enzyme recognition sequence and the oligonucleotide 11 at the 3' terminus of the−strand of the cDNA fragment 3 and to the restriction enzyme recognition sequence and the oligonucleotide 11 at the 3' terminus of the+strand of the cDNA fragment 3. Thus, the primer set 23 amplifies DNA fragment 5 with the oligonucleotide 11 ligated at the 3' terminus thereof.

The oligonucleotide 12 of a known nucleotide sequence is complementary to the sequence of the modules in the order of III-IV-I-II in the primer 22 belonging to the primer set 24. The oligonucleotide 12 is ligated in the digestion site of the cDNA fragment 4 as a digestion product with the restriction enzyme Sau3A I recognizing the nucleotide sequence 5'-GATC-3' to digest the site ↓GATC. The oligonucleotide 12 is ligated in the 3' terminus of the sequence of the 4 nucleotides, namely 5'-GATC-3' at the 3' terminus of the −strand of the cDNA fragment 4 and in the 3' terminus of the sequence of the 4 nucleotides, namely 5'-GATC-3' at the 3' terminus of the+strand of the cDNA fragment.

The primer set 24 hybridizes to the restriction enzyme recognition sequence and the oligonucleotide 12 at the 3' terminus of the−strand of the cDNA fragment 4 and to the restriction enzyme recognition sequence and the oligonucleotide 12 at the 3' terminus of the +strand of the cDNA fragment 4. Thus, the primer set 24 amplifies DNA fragment 6 with the oligonucleotide 12 ligated at the 3' terminus thereof.

The individual primers of the primer sets 23, 24 are independently labeled with fluorophores FA25 and FB26, respectively.

Figure 2A:
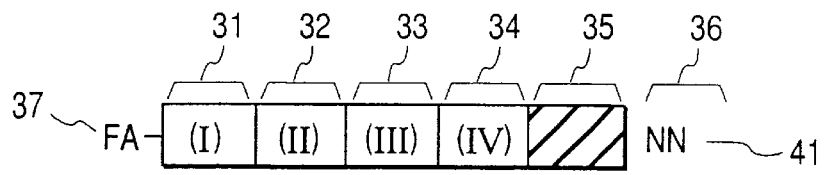
FIGS. 2A and 2B are figures depicting the structures of the primers of Example 1 of the invention and also showing the structures of oligonucleotides of known nucleotide sequences.
Figure 2B:
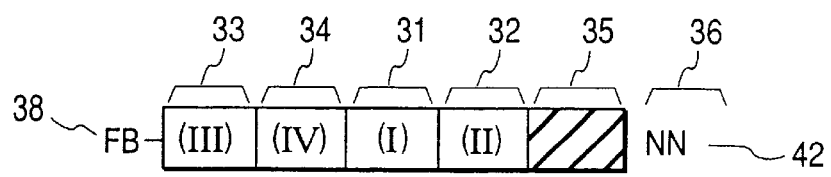

FIG. 2A depicts the structure of primer 41. The primer 41 is composed of the sequence I-II-III-IV of 4 modules in the order starting from the 5' terminus, each module being composed of 4 nucleotides, restriction enzyme recognition nucleotide sequence 35 and selective nucleotide sequence 36 composed of 2 nucleotides, wherein the sequence I-II-III-IV is the sequence 31-32-33-34. FIG. 2B depicts the structure of primer 42. The primer 42 is composed of the sequence III-IV-I-II of 4 modules in the order starting from the 5' terminus, each module being composed of 4 nucleotides, restriction enzyme recognition nucleotide sequence 35 and selective nucleotide sequence 36 composed of 2 nucleotides, wherein the sequence III-IV-I-II is the sequence 33-34-31-32.

Figure 2C:
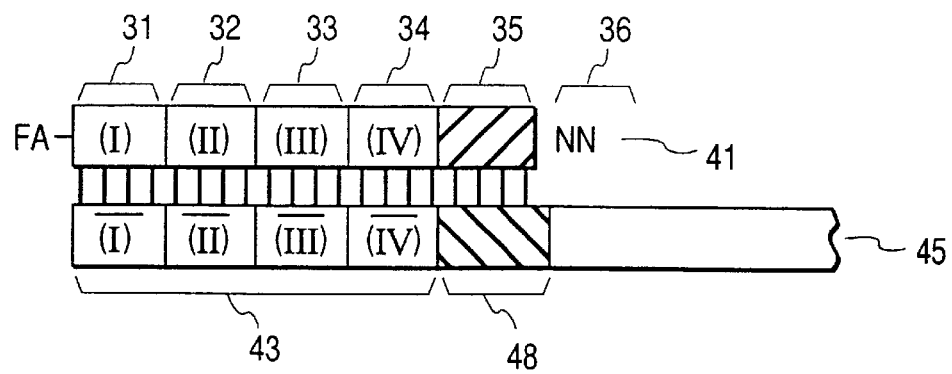
FIGS. 2C and 2D are figures depicting the hybridization of the primers of Example 1 of the invention and DNA fragments.
Figure 2D:
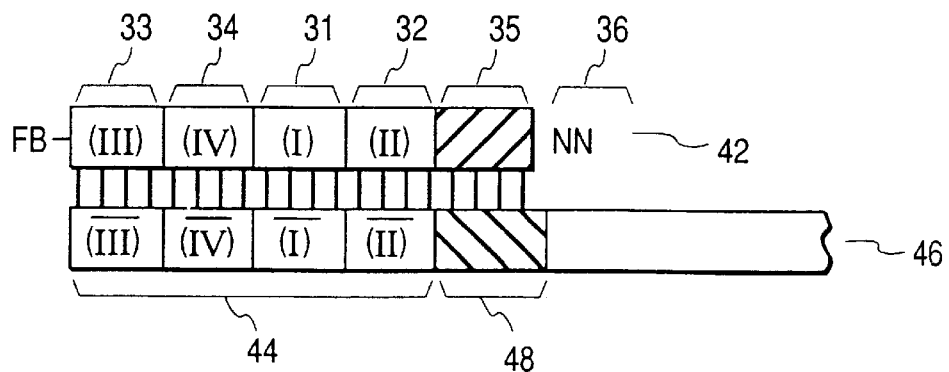

FIG. 2C depicts the state of the complex of primer 41/DNA fragment 45; and FIG. 2D depicts the state of the complex of primer 42/DNA fragment 46. In FIGS. 2C and 2D, the nucleotide sequence of the modules 31, 32, 33 and 34 in this order is complementary to the oligonucleotide 43 and the nucleotide sequence of the modules 33, 34, 31 and 32 in this order is complementary to the oligonucleotide 44. The primers 41 and 42 are composed of the same modules 31, 32, 33, 34, the restriction enzyme recognition nucleotide sequence 35 and the selective nucleotide sequence 36 composed of two nucleotides; although the orders of the modules in these sequences are different from each other, these primers are at the same $T_m$ value. The primer 41 hybridizes to the 3' terminus of the DNA fragment 45 with the oligonucleotide 43 complementary to the primer 41, the oligonucleotide 43 being ligated to the 3' terminus of the restriction enzyme-digested site 48. The primer 42 hybridizes to the 3' terminus of the DNA fragment 46 with the oligonucleotide 44 complementary to the primer 42, the oligonucleotide 44 being ligated to the 3' terminus of the restriction enzyme-digested site 48.

Because the primers 41, 42 are at the same $T_m$ value, these primers hybridize to the oligonucleotides 43, 44 at the same reaction efficiency, with no hybridization to each other because these primers are not complementary to each other, the primers never suppress each other's reaction, whereby PCR can be facilitated in one reaction tube. Because the primers 41, 42 are labeled with the different fluorophores 37, 38, respectively, the DNA fragments amplified by PCR with the primers 41, 42 are therefore labeled then with the different fluorophores, which are detected by electrophoresis based on the difference in fluorescent wave length.

FIG. 1 shows a forward primer and a reverse primer selected from the primer set 23 so as to amplify the DNA fragment 5, as well as a forward primer and a reverse primer selected from the primer set 24 so as to amplify the DNA fragment 6. The sample DNA fragments 5,6 are divided in a reaction tube. The selected 4 primers in total are placed in the reaction tube containing the sample DNA fragments 5,6, followed by addition of a reaction solution of thermostable DNA polymerase, substrate DNTP and a reaction buffer, for PCR. By PCR, amplification reaction is promoted at a temperature cycle composed of three steps, namely heat denaturation, re-annealing and elongation.

At the heat denaturation step, the reaction solution is heated at about 94° C., so that the cDNA fragments (double-stranded DNAs) 5, 6 are separated as cDNA fragment+strands 7, 8 and cDNA fragment−strands 9, 10 in the form of single-stranded DNA fragment. At the re-annealing step, the reaction solution is kept at about 60° C. Because the concentrations of the primers are higher than the concentrations of the cDNA fragments+stands 7, 8 and the cDNA fragments−strands 9, 10, the annealing of the primers with the cDNA fragments progresses more preferentially than the re-annealing of the cDNA fragment+strand 7 with the cDNA fragment−strand 9 or the re-annealing of the cDNA fragment+strand 8 with the cDNA fragment−strand 10. The annealing of the primer 21 with the cDNA fragment+strand 7 and the annealing of the primer 21 with the cDNA fragment−strand 9 generates a double-stranded DNA; and the annealing of the primer 22 with the cDNA fragment+strand 8 and the annealing of the primer 22 with the cDNA fragment−strand 10 generates a double-stranded DNA. By the DNA polymerase, the primers 21, 22 generating the double strands together with the cDNA fragments are elongated at the elongation step, so that the DNA fragments are amplified. By PCR, amplification progresses when such oligonucleotide is elongated, starting from both the termini of the cDNA fragments. When only the +strand or −strand of the DNA fragment is elongated, the thermal cycle repeated at a number n induces amplification only by n-fold, below the detection sensitivity. When both the + and −strands are elongated, amplification by $2^n$ fold occurs.

Because the primers 21,22 are labeled with the fluorophores, PCR products 17, 18 generated by amplification with the primers 21, 22 are also labeled with the fluorophores. Accordingly, the PCR products can be assayed by using electrophoresis systems of fluorophore detection type and the like. On laser irradiation of the PCR products separated by electrophoresis, the fluorophores 25, 26 can emit fluorescence at different wave lengths, which are detected through image splitting prisms and filters with a two-dimensional detector so as to identify which fluorophore emits the fluorescence. The resulting detected signals are derived from the PCR amplified products of the cDNA fragments recovered by restriction digestion of the sample cDNA. Hence, the fragment length and fluorescent intensity of an amplified DNA fragment can identify each type of various mRNAs.

Figure 3:
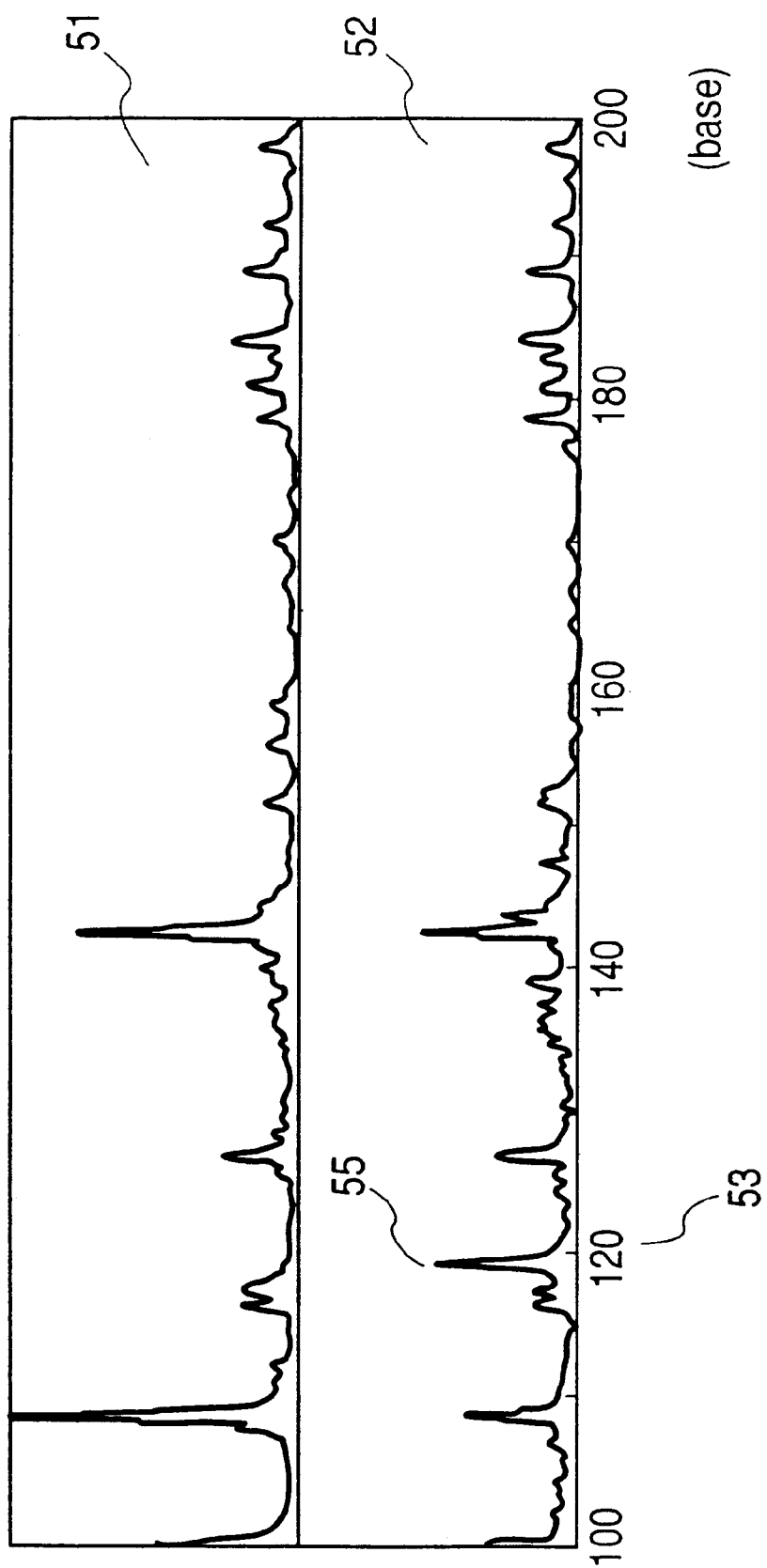
FIG. 3 shows parts of electropherograms of expression profiling by using the primers of Example 1 of the invention.

FIG. 3 depicts electropherograms (electrophoretic patterns) of expression profiling recovered by using the primers of Example 1 of the invention, wherein the parts 51, 52 of the electropherograms are shown in a manner corresponding to nucleotide length 53. In Example 1, genes expressed in rat liver and kidney are compared to each other.

The electropherogram 51 can be recovered by electrophoresis of the PCR amplified products with the primer 21, while the electropherogram 52 can be recovered by electrophoresis of the PCR amplified products with the primer 22.

Most of the peaks in the electropherograms 51, 52 are detected at the same positions, indicating that the peaks represent genes commonly expressed in both the tissues. In one of the electropherograms, namely 52, peak 55 is detected, which is derived from a gene specifically expressed at an expression state different from the other tissue. The genes commonly expressed in the two tissues are detected at good reproducibility on the two electropherograms. PCR in one reaction tube by using primers of plural primer sets readily enables the comparison of PCR products in an accurate manner, with no requirement of PCR in separate manners by using primers of individual primer sets.

EXAMPLE 2

In Example 2, PCR products are assayed by using a probe array immobilizing numerous types of cDNA probes with nucleotide sequences complementary to gene sequences.

Figure 4:
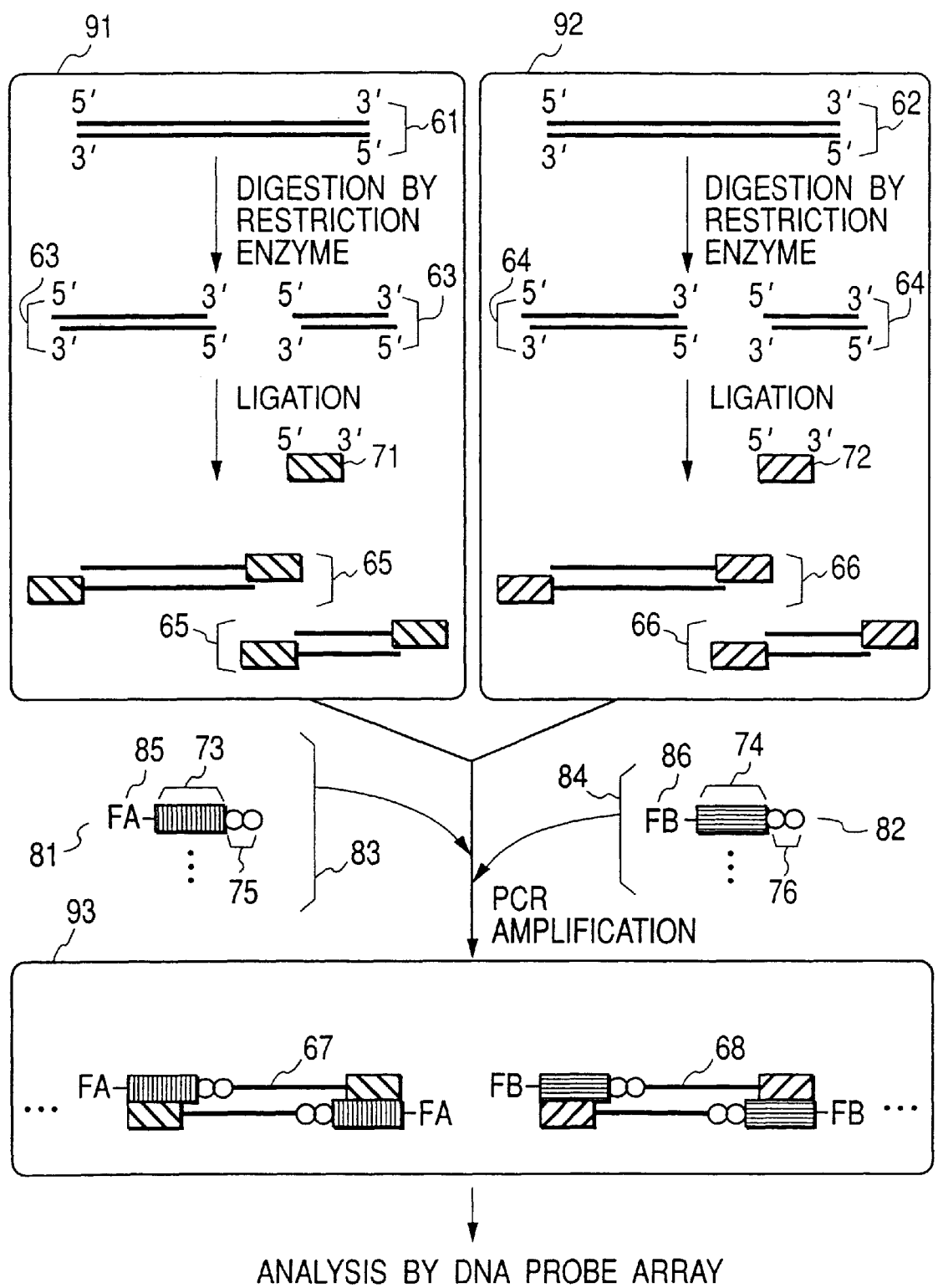
FIG. 4 is a flowchart of the procedures of expression profiling in Example 2 of the invention.

FIG. 4 shows the flowchart of the procedures for expression profiling of Example 2 of the invention. In the same manner as in Example 1, cDNA mixtures 61, 62 as samples prepared from RNAs extracted from different yeast strains are placed in reaction tubes 91, 92 (in the FIG. 4, only one cDNA mixture is shown) and are digested with a class II restriction enzyme. The class II restriction enzyme was Mbo I recognizing the sequence 5'-GATC-3' and digesting the site ↓GATC. Oligomers 71, 72 are ligated to the resulting cDNA fragments 63, 64, to prepare cDNA fragments 65, 66 with the oligomers 71, 72 ligated at the termini thereof. Then, the cDNA fragments 65, 66 are mixed together; a part of the resulting mixture solution is placed in PCR tube 93, which is used as template DNA fragments for PCR.

As a PCR primer, primer 81 composed of common nucleotide sequence 73 composed of 4 module sequences, I. ACAA, II. GACG, III. ATCA and IV. GCAG, and the restriction enzyme recognition nucleotide sequence GATC, and selective nucleotide sequence NN 75 being composed of two nucleotides NN and recognizing two nucleotides subsequent to the restriction enzyme recognition sequence GATC (NN corresponds to any one of A, C, G and T) is prepared. The primer 81 is of the nucleotide sequence of SQ ID No. 3.

SQ ID No. 3

5'-ACAAGACGATCAGCAGGATCNN-3'

NN corresponds to any one of A, C, G and T; the primer 81 composes primer set 83 composed of 16 primers. Furthermore, primer 82 is prepared, which is composed of common nucleotide sequence 74 composed of 4 module sequences in the order of I-IV-III-II and the restriction enzyme recognition nucleotide sequence GATC, and selective nucleotide sequence NN 76 composed of two nucleotides (NN corresponds to any one of A, C, G and T). The primer 82 is of the nucleotide sequence of SQ ID No. 4. NN corresponds to any one of A, C, G and T; the primer 82 composes the primer set 84 composed of 16 primers, like the primer 81.

SQ ID No. 4

5'-ACAAGCAGATCAGACGGATCNN-3'

The oligonucleotide 71 of a known nucleotide sequence is complementary to the sequence of the modules in the order of I-II-III-IV in the primer 81 belonging to the primer set 83. The oligonucleotide 72 of a known nucleotide sequence is complementary to the sequence of the modules in the order of I-IV-III-II in the primer 82 belonging to the primer set 84. Thus, the primer set 83 amplifies DNA fragment 65 with the oligonucleotide 71 ligated at the 3' terminus thereof, while the primer set 84 amplifies DNA fragment 66 with the oligonucleotide 72 ligated at the 3' terminus thereof.

The individual primers of the primer sets 83, 84 are independently labeled with fluorophores FA85 and FB86, respectively.

A forward primer and a reverse primer are selected from the primer set 83 so as to amplify the DNA fragment 65; a forward primer and a reverse primer are selected from the primer set 84 so as to amplify the DNA fragment 66. The selected 4 primers in total are placed in reaction tube 93 containing the sample DNA fragments 65,66 divided therein, followed by addition of a reaction solution of thermostable DNA polymerase, substrate DNTP and a reaction buffer, for PCR. Subsequently, PCR products 67, 68 are assayed by using a DNA probe array with numerous types of cDNA probes immobilized on a glass plate.

Figure 5:
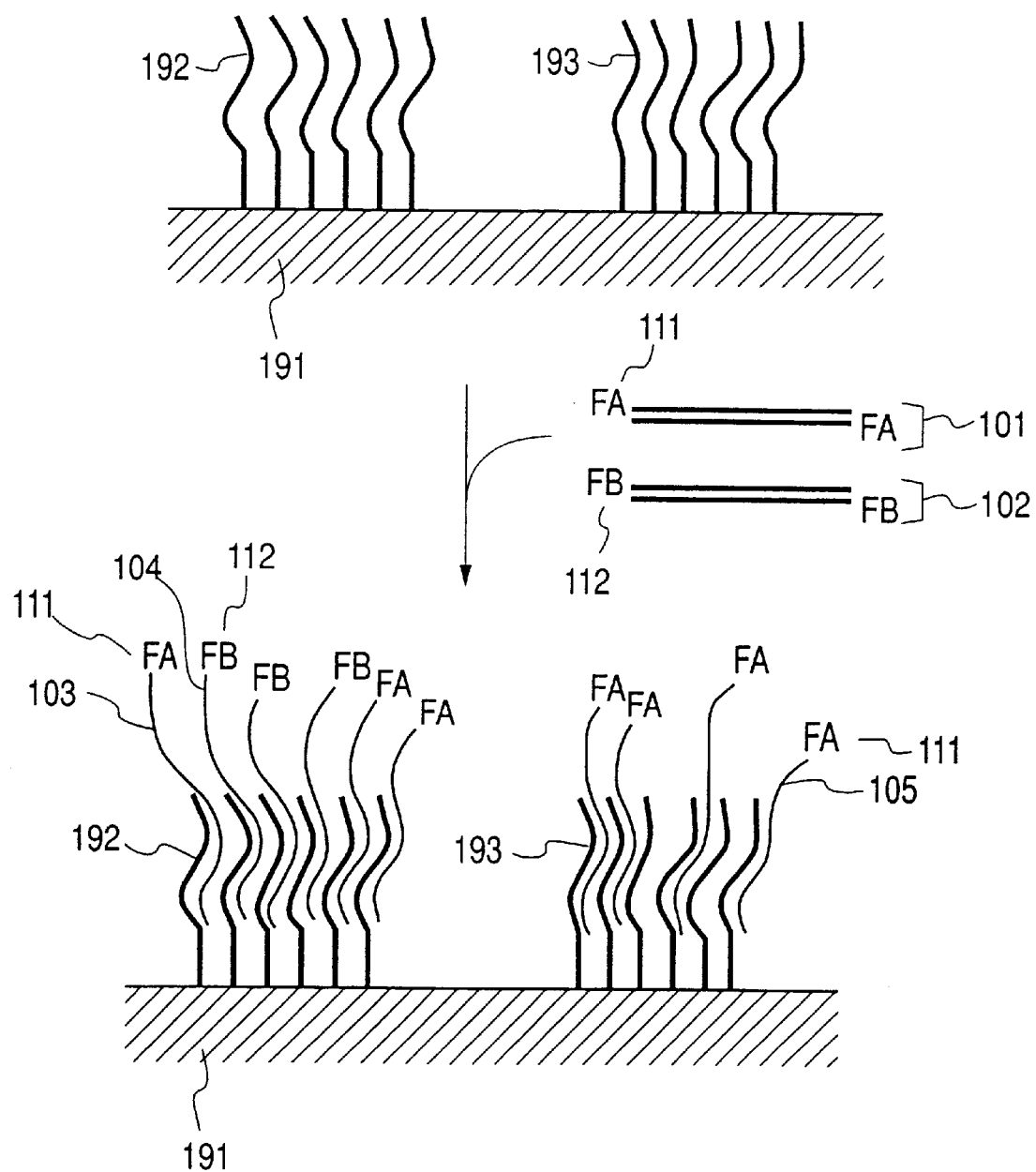
FIG. 5 is a flowchart of the procedures of expression profiling by using DNA probe array in Example 2 of the invention.

FIG. 5 is a flowchart depicting the procedures of expression profiling by using the DNA probe array. In FIG. 5, 191 is glass plate; 192, 193 are DNA probes individually immobilized on the glass plate. Within a zone of several square centimeters on the glass plate 191 are two-dimensionally immobilized several tens to several hundreds of DNA probes in groups divided, depending on the types. On the glass plate are arranged PCR products 101, 102 labeled with fluorophores FA111, FB112, for hybridization to the DNA probes. Thereafter, the plate was rinsed, to wash off PCR products with no hybridization. On a glass plate section with DNA probe 192 immobilized thereon, PCR products with no hybridization to the DNA probe 192 are rinsed off among the PCR products, while the complementary PCR products 103, 104 hybridize to the DNA probe 192. In the same manner, PCR products with no hybridization to the DNA probe 193 are rinsed off among the PCR products, while the complementary PCR product 105 hybridizes to the DNA probe 193. Among PCR products 101, PCR products 103, 105 are DNA fragments hybridizing to the DNA probes 192, 193 on the DNA probe array and being labeled with the fluorophore FA111. Alternatively, the PCR product 104 is a DNA fragment hybridizing to the DNA probe 192 on the DNA probe array and being labeled with the fluorophore FB112.

Figure 6:
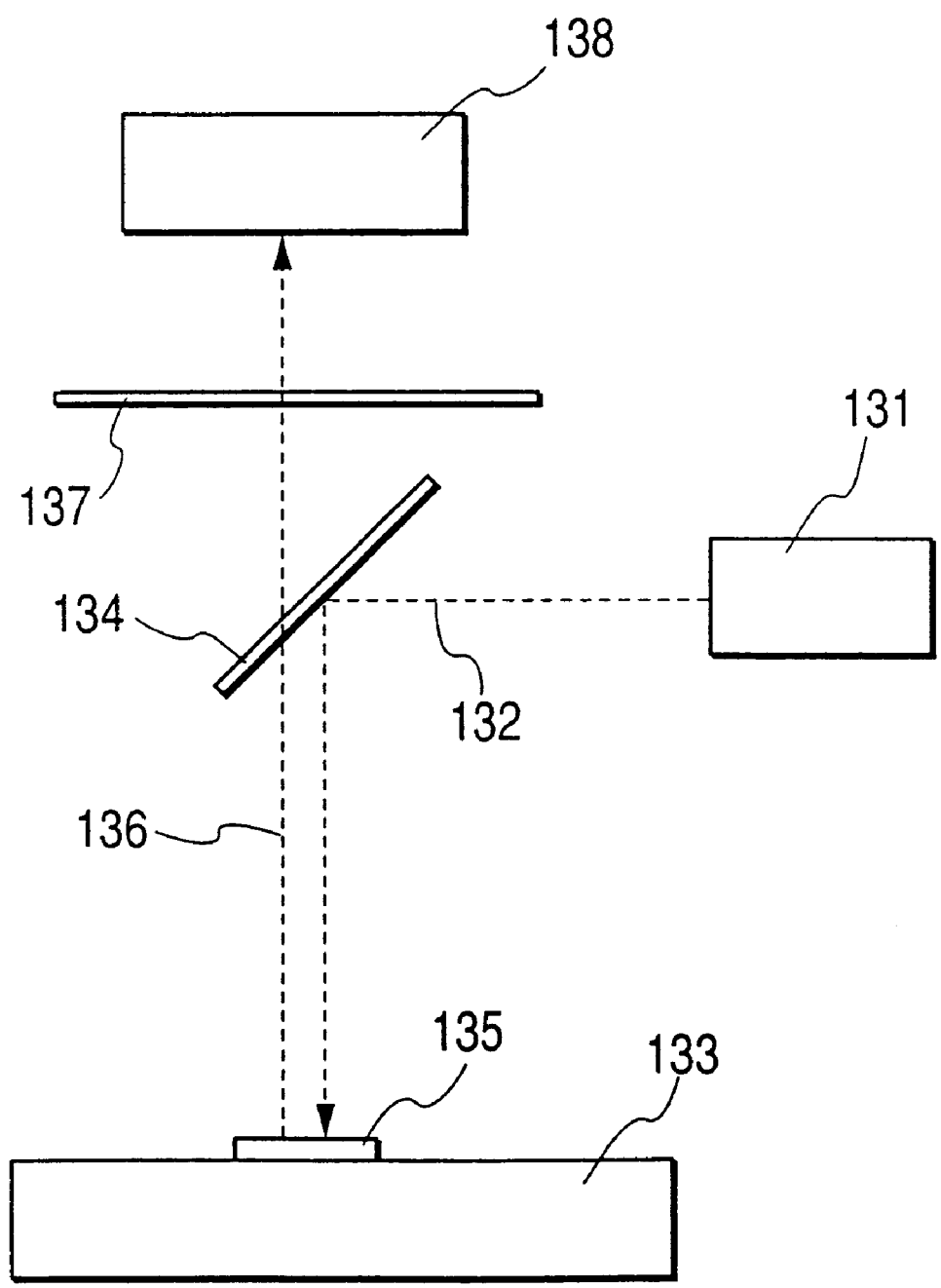
FIG. 6 shows the mechanistic composition of a fluorescent microscope detecting a sample on DNA probe array in Example 2 of the invention.

FIG. 6 is a figure depicting the mechanistic composition of a fluorescent microscope for detecting the samples on the DNA probe array in Example 2 of the invention. By using the laser microscope of FIG. 6, PCR products hybridizing to the DNA probe array can be detected. Laser beam 132 from laser source 131 is reflected on dichroic mirror 134, to irradiate DNA probe array 135 arranged on microscope stage 133. Fluorescence 136 emitted from the fluorophore arranged on the microscope stage 133 is passed through filter 137 to be detected with detector 138. In Example 2, two types of fluorophores FA and FB are used, so two types of filters are prepared for different wave lengths to detect fluorescence at the individual fluorescent wave lengths.

Figure 7:
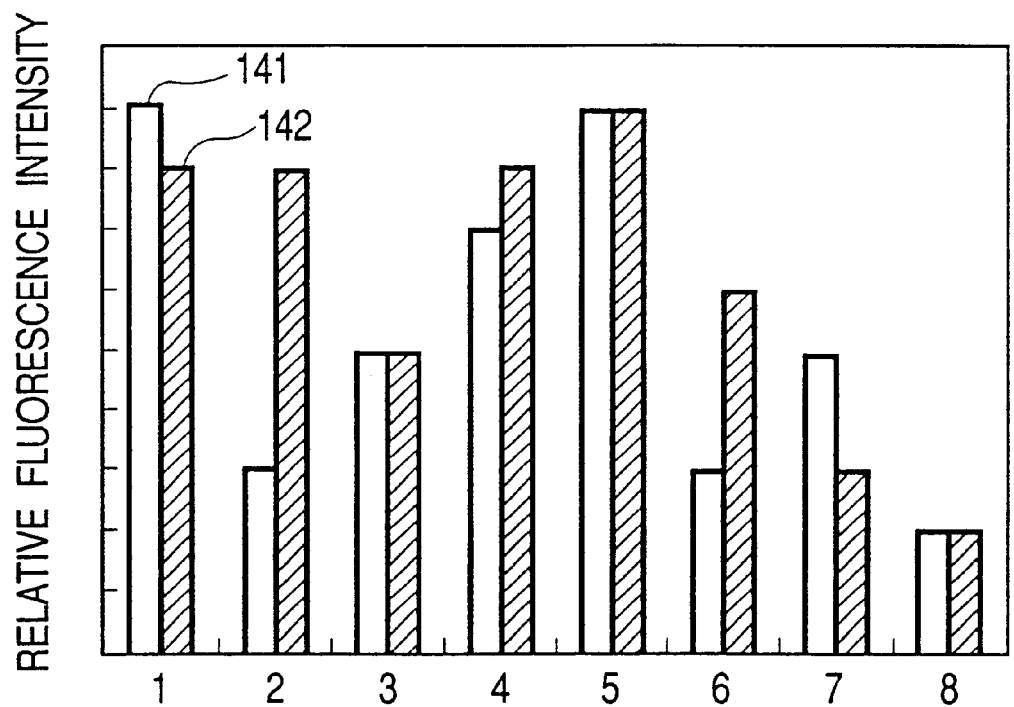
FIG. 7 shows fluorescent intensities in bar graph from a DNA probe array for expression profiling using the primers of Example 2 of the invention.

FIG. 7 shows fluorescent intensities in bar graph from a DNA probe array, depicting expression profiling recovered by using the primers of Example 2 of the invention. As shown in FIG. 7, plural types of DNA fragments can be compared to each other, by comparing the fluorescent intensities detected at positions of individual immobilized DNA probes on the DNA probe array. In FIG. 7, the longitudinal axes 141, 142 represent fluorescent intensities from PCR products labeled with different fluorophores. The crosswise axis represents the number of the position of each DNA probe immobilized on the DNA probe array. The comparison of the fluorescent intensity at each wave length at the position of one DNA probe on the DNA probe array enables the comparison of DNA fragments extracted from plural samples. Because cDNA fragments are simultaneously PCR amplified in one reaction tube, these fragments are readily assayed in a comparative manner with no concern about PCR reproducibility.

In accordance with the invention, at least two or more sets of primers are used for PCR in one reaction tube. Individual primers are labeled with different fluorophores and thus function independently. So as to amplify one sample DNA with a first set of primers and to amplify the other sample DNA with a second set of primers, oligonucleotides with complementary nucleotide sequences to the individual primers are ligated to the individual sample DNAs, which are then placed in one reaction tube for PCR. Plural primers for use in PCR should have the same $T_m$ value to eliminate the difference in reaction efficiency among the individual primers. So as to allow plural primers to have the same $T_m$ value, different sequence orders of plural modules are ligated in the individual primers, each module being composed of 4 to 6 nucleotides, to prepare plural primers. So as to avoid the modification of the nucleotide sequence in the linking regions between individual modules even after exchange of the sequence order of the modules that have same nucleotide species, both the termini of each module are composed of the same nucleotide species. By using plural modules at almost the same $T_m$ value and with no difference in PCR reaction efficiency, plural sample DNAs are subjected to PCR in one reaction tube, with no variation of PCR.

Reference numbers in the individual figures are now described below.

1, 2, 61, 62: sample cDNAs in mixture
3,4,63,64: cDNA fragments digested by restriction enzyme
5,6: cDNA fragment with an oligonucleotide of a known nucleotide sequence being ligated at the terminus thereof
7,8: cDNA fragment+strand
9,10: cDNA fragment−strand
11, 12: oligonucleotide of a known nucleotide sequence
13, 14, 73, 74: common nucleotide sequence
15, 16, 36, 75, 76: selective nucleotide sequence
17, 18, 67, 68, 101, 102: PCR amplified products
21, 22, 41, 42, 81, 82: primer
23, 24, 83, 84: primer set
25, 26, 37, 38, 85, 86, 111, 112: fluorophore
27, 28, 29, 91, 92, 93: reaction tube
31, 32, 33, 34: sequence of modules (module sequence)
35: recognition site of restriction enzyme
43, 44: oligonucleotide
45, 46: DNA fragment
48: restriction enzyme digested site
51; 52: electropherogram
53: base length
55: peak derived from specifically expressed gene
65, 66: cDNA fragment with an oligomer of a known nucleotide sequence being ligated at the terminus thereof
71, 72: oligomer of a known nucleotide sequence
103, 104, 105: PCR products hybridizing to DNA probe
131: laser source
132: laser beam
133: microscope stage
134: dichroic mirror
135: DNA probe array
136: fluorescence
137: filter
138: detector
141, 142: fluorescent intensity of PCR products
191: glass plate
192, 193: DNA probe

SEQUENCE LISTING

<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: n = a, t, c, or g

<400> SEQUENCE: 1
tcatcacctt ctccacgatc nn                                    22

-continued

```
<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: n = a, t, c, or g

<400> SEQUENCE: 2
ttctccactc atcaccgatc nn                                              22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: n = a, t, c, or g

<400> SEQUENCE: 3
acaagacgat cagcaggatc nn                                              22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: n = a, t, c, or g

<400> SEQUENCE: 4
acaagcagat cagacggatc nn                                              22
```

Sequencing Listing Free Text
(1) OTHER INFORMATION FOR SEQ ID NO.1
DNA primer used for PCR (n is a or c or g or t).
(2) OTHER INFORMATION FOR SEQ ID NO. 2
DNA primer used for PCR (n is a or c or g or t).
(3) OTHER INFORMATION FOR SEQ ID NO.3
DNA primer used for PCR (n is a or c or g or t).
(4) OTHER INFORMATION FOR SEQ ID NO.4
DNA primer used for PCR (n is a or c or g or t).

What is claimed is:

1. A method for assaying DNA fragments in a mixture comprising:
   (1) ligating oligomers having known different nucleotide sequences to the 3' termini of DNA fragments in each of the DNA fragment groups, the DNA fragments in each of the DNA fragment groups being prepared, respectively, from each of sample DNAs, and each of the oligomers being preselected corresponding to each of the DNA fragment groups;
   (2) mixing, in one receptacle, the DNA fragments ligated with the oligomers in the DNA fragment groups;
   (3) performing a polymerase chain reaction to obtain amplified DNA fragments, in the one receptacle, simultaneously, using the mixture of DNA fragments ligated with the oligomers as templates, and using primers each being complementary to each of the oligomers being ligated to the DNA fragments in each of the DNA fragment groups, and each of the primers being preselected corresponding to each of the DNA fragment groups; and
   (4) detecting the amplified DNA fragments; wherein:
   the primers comprise plural module sequences;
   aligning orders of the plural module sequences of the primers are different from one another;
   each of the aligning orders of each the plural module sequences is preselected corresponding to each of the DNA fragment groups;
   each of the plural module sequences is composed of 4 to 6 nucleotides and has the same nucleotide species at the 3' terminus and 5' terminus thereof;
   the plural module sequences have known different nucleotide sequences, respectively;
   the primers have the same length, melting temperature, and composition of nucleotides;
   the primers have known different nucleotide sequences, respectively; and
   the aligning orders of the plural module sequences are obtained by replacing the aligning orders of two module sequences which have the same nucleotide species at the 3' terminus and 5' terminus thereof; and wherein:
   the primers are labeled with different fluorophores being preselected corresponding to each of the DNA fragment groups; and
   the amplified DNA fragments are labeled with the different fluorophores corresponding to each of the DNA fragment group.

2. The method of claim 1 wherein the amplified DNA fragments are detected by electrophoresis.

3. The method of claim 1 wherein the amplified fragments are detected by using a DNA probe array immobilizing plural types of DNA probes having nucleotide sequences complementary to the DNA fragments of the DNA fragment groups thereon.

4. Primers for use in a method for assaying DNA fragments in a mixture, wherein the primers comprise:
- plural module sequences having known different nucleotide sequences, respectively;
- orders of the plural module sequences of the primers having alignments different from one another;
- each of the plural module sequences comprising 4 to 6 nucleotides and the same nucleotide species at the 3' terminus and 5' termini thereof; and
- the different alignment orders of the plural module sequences being obtained by replacing the alignment orders of two module sequences that have the same nucleotide species at the 3' and 5' termini thereof;

wherein the primers:
- have the same length, melting temperature, and composition of nucleotides;
- have known different sequences of nucleotides, respectively; and
- are labeled with different fluorophores.

* * * * *